(12) United States Patent
Austin

(10) Patent No.: US 8,607,366 B2
(45) Date of Patent: Dec. 17, 2013

(54) GARMENT FOR SECURING AN EXTERNAL PORTION OF A CATHETER

(76) Inventor: Emily Austin, Phoenix, MD (US)

(*) Notice: Subject to any disclaimer, the term of this patent is extended or adjusted under 35 U.S.C. 154(b) by 43 days.

(21) Appl. No.: 12/889,923

(22) Filed: Sep. 24, 2010

(65) Prior Publication Data

US 2012/0078190 A1 Mar. 29, 2012

(51) Int. Cl.
*A41F 19/00* (2006.01)
(52) U.S. Cl.
USPC ..................... 2/300; 2/80; 604/174
(58) Field of Classification Search
USPC .................. 604/174, 179, 180; 2/80, 300
See application file for complete search history.

(56) References Cited

U.S. PATENT DOCUMENTS

| | | | |
|---|---|---|---|
| 4,666,432 A | 5/1987 | McNeish et al. | |
| 5,048,122 A | 9/1991 | Prieur | |
| 5,755,798 A | 5/1998 | Papavero et al. | |
| 6,206,854 B1 | 3/2001 | Weaver | |
| 6,296,164 B1 | 10/2001 | Russo | |
| 6,477,710 B1 | 11/2002 | Ojoyeyi | |
| 6,579,268 B1 * | 6/2003 | Loining | 604/174 |
| 6,647,552 B1 * | 11/2003 | Hogan | 2/114 |
| 6,681,404 B1 | 1/2004 | Adlard et al. | |
| 7,000,261 B1 * | 2/2006 | Loffredo | 2/400 |

* cited by examiner

*Primary Examiner* — Kevin C Sirmons
*Assistant Examiner* — Brandy S Lee
(74) *Attorney, Agent, or Firm* — Medler Ferro PLLC

(57) ABSTRACT

A garment includes a vertical opening and a transverse flap on the front panel thereof for securing an external portion of a central line or catheter having at least two distal lumens or branches. The external portion of the catheter extends through a gap between a pair fasteners of the vertical opening. In order to secure the catheter, the flap includes a stopper that is fastened to front panel such that the stopper is located between the distal branches of the catheter. If one or both of the distal branches are pulled or tugged, a junction or transition area of the catheter is pressed against the stopper and limits further motion of the catheter to prevent dislodgement thereof. The flap further includes a series of fasteners for releasably coupling a free edge thereof onto the front panel to house the external portion of the catheter under the closed flap.

20 Claims, 5 Drawing Sheets

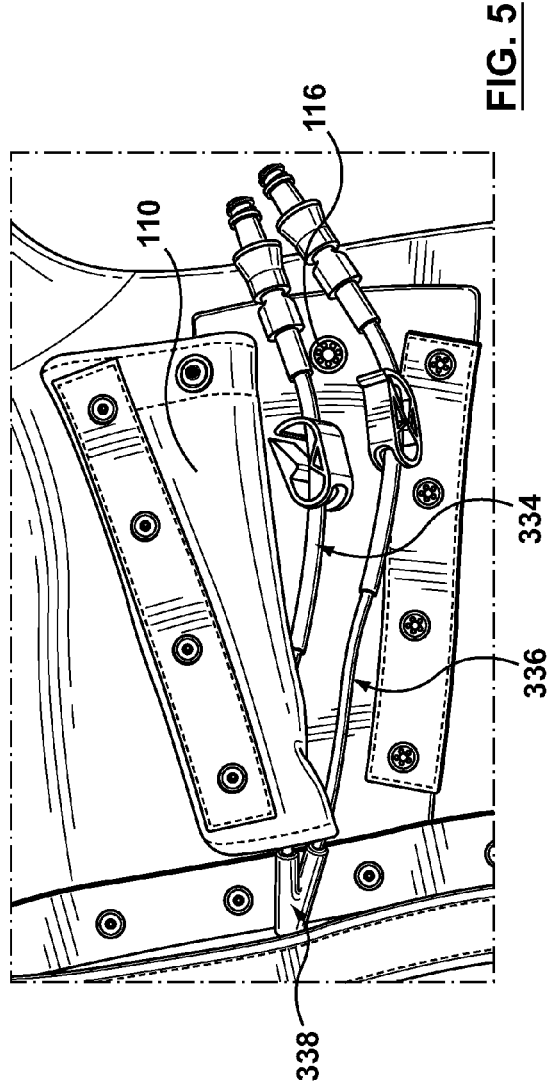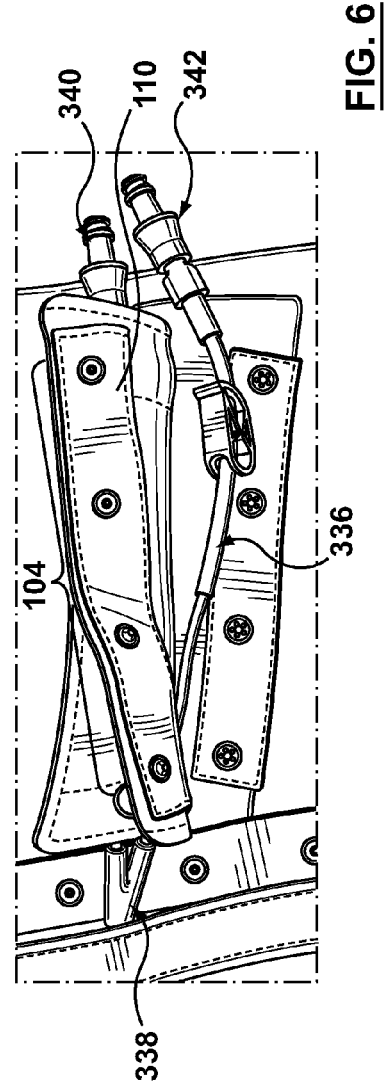

GARMENT FOR SECURING AN EXTERNAL PORTION OF A CATHETER

FIELD OF THE INVENTION

Embodiments hereof relate to a garment for securing an external portion of a surgically implanted catheter.

BACKGROUND OF THE INVENTION

A central venous catheter, also known as a central line, is a catheter placed into a large vein in the neck including the internal jugular vein or external jugular vein, in the chest including the subclavian vein, or in the groin including the femoral vein. A central line is used to administer medication or fluids, obtain blood tests, and/or directly obtain cardiovascular measurements such as the central venous pressure. Such catheters are designed for long-time use in the order of weeks, months and even years in order to avoid many needle punctures that may cause pain, fear, anxiety and/or risks of skin infections. For example, a cancer patient requires frequent blood tests or chemotherapy and thus typically has a surgically implanted catheter. During chemotherapy, a surgically implanted catheter permits subsequent patient care on an outpatient basis. The patient returns to a medical facility for administration of the therapeutic agent through the catheter without having a needle inserted into a vein each time. Moreover, an implanted catheter makes it possible for the patient or an attendant to perform certain other procedures at home thereby reducing the number of times the patient must leave his or her residence. This is particularly advantageous when the patient is a small child.

A Hickman® catheter is a specific type of long-term catheter that is generally flexible and is comprised of a small permanent rubber internal tubing portion that is surgically implanted into the right atrium of the heart, an external tubing portion extending from the exit site where the internal tubing portion extends from the patient's body, and an enlarged capped portion attached to the end of the external tubing portion. Such implants necessitate a surgical procedure normally under general anesthesia. Typically the internal tubing portion is inserted under the skin of the chest wall and into a large vein that leads into the heart. The external tubing must be secured to the patient, normally by padding and tape adhered to the skin, in order to assure that the patient does not dislodge the catheter by inadvertent manipulation of the catheter line. The external portion of the catheter has in prior practice been taped directly to the skin of the body with the capped end or ends positioned upwardly.

Securing the external portion of the catheter to the patient with tape to prevent displacement and/or dislodgment of the catheter has disadvantages. Most importantly, securement via tape may not sufficient hold the catheter tubing onto the patient. For example, when the patient is a small child, the child may play with or rip the tape away from the skin causing irritation and increasing the risk of infection. Sometimes a child will open the catheter line and suffer blood loss or permit air to enter into the bloodstream. Children have been known to dislodge the catheter itself or even pull it out thereby imposing a serious medical condition, sometimes requiring another surgical procedure under unfavorable, emergency conditions. As a result, medical personnel sometimes are reluctant to implant catheters in small children unless there is some assurance that the child will not play with the catheter thereby compounding the various risks normally associated with such implants. This generally means some assurance that the child will always be watched. Even when the patient is an adult, the tape may not afford the desired freedom of movement because the patient constantly may fear dislodgment of the catheter from its exit site on the body.

In addition, the tape used to secure the external portion of the catheter must be removed and replaced at least once a day. More particularly, each time the capped free end of the catheter is to be used, it is first necessary to remove the tape that secured the externally extending tubing portion to the body. Since the tube has to be flushed out at least once a day to prevent clogging, this means that the tape has to be removed at least once a day and often more for other required purposes. Frequent removal and replacement of the tape from the body generally results in sores and/or irritation to the body and thus, discomfort to the patient.

Garments for holding and/or storing catheters have evolved. These garments have lessened or eliminated many of the disadvantages inherent with the tape-retention method for the catheter tubes, but there is still a need in the art to develop and/or improve a garment that secures an external portion of a central line or catheter, especially for sensitive and/or special need patients such as children.

BRIEF SUMMARY OF THE INVENTION

Embodiments hereof relate to a garment for securing an external portion of a biluminal catheter having at least two distal branches. The garment includes a vertical opening extending along a front panel of the garment, the opening including a series of fasteners for releasably closing the opening. The fasteners have spaces therebetween for allowing the catheter to pass through. The garment also includes a flap coupled to the front surface that extends across the front panel in a direction generally transverse the vertical opening. The flap is positioned adjacent to the vertical opening and includes a series of fasteners for releasably coupling a free edge of the flap onto the front panel. A stopper is coupled to the flap and may be releasably fastened to the garment between the distal branches of the catheter.

Embodiments hereof also relate to a method of securing a catheter having a proximal end implanted within a patient and at least two external distal branches. The two external distal branches of the catheter extend or pass through a space between a pair of fasteners that releasably close a vertical opening that extends along a front panel of a garment. The garment further includes a flap positioned adjacent to the vertical opening that extends across the garment in a direction generally transverse the vertical opening. A stopper located on the flap is fastened to the front panel of the garment such that the stopper is located between the distal branches of the catheter. The stopper reduces the risk of unintentional dislodgement of the catheter.

BRIEF DESCRIPTION OF DRAWINGS

The foregoing and other features and advantages of the invention will be apparent from the following description of embodiments hereof as illustrated in the accompanying drawings. The accompanying drawings, which are incorporated herein and form a part of the specification, further serve to explain the principles of the invention and to enable a person skilled in the pertinent art to make and use the invention. The drawings are not to scale.

FIGS. 4-6 illustrate a method of securing the biluminal catheter of FIG. 3 within the garment of FIG. 1 according to an embodiment hereof.

DETAILED DESCRIPTION OF THE INVENTION

Specific embodiments hereof are now described with reference to the figures, wherein like reference numbers indicate identical or functionally similar elements. The following detailed description is merely exemplary in nature and is not intended to limit the invention or the application and uses of the invention. Furthermore, there is no intention to be bound by any expressed or implied theory presented in the preceding technical field, background, brief summary or the following detailed description. As used herein, the terms "distal" and "proximal" refer to a position or direction relative to the patient. "Distal" or "distally" are a position distant from or in a direction away from the patient. "Proximal" and "proximally" are a position near or in a direction toward the patient. In addition, as used herein, an "internal" portion of a catheter is meant to refer to the portion of the catheter that is surgically implanted within a patient's body up to an exit site, while an "external" portion of a catheter is meant to refer to the portion of the catheter that is not implanted within a patient's body and extends from the exit site.

Figure 1:
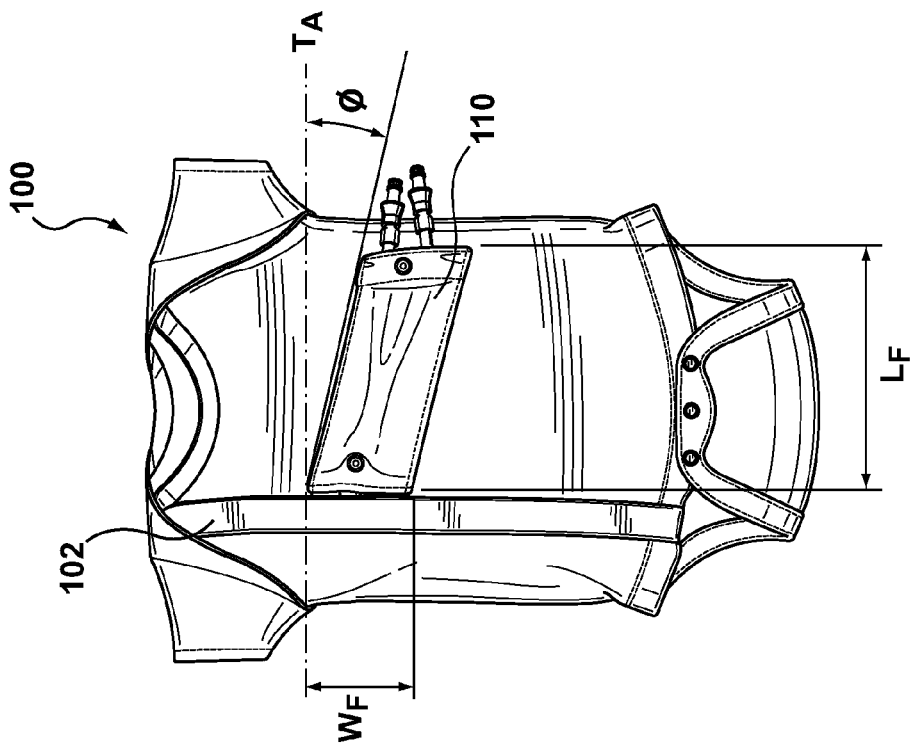
FIG. 1 is an image of a garment for securing an external portion of a catheter, wherein a vertical opening and a flap of the garment are open.
Figure 2:
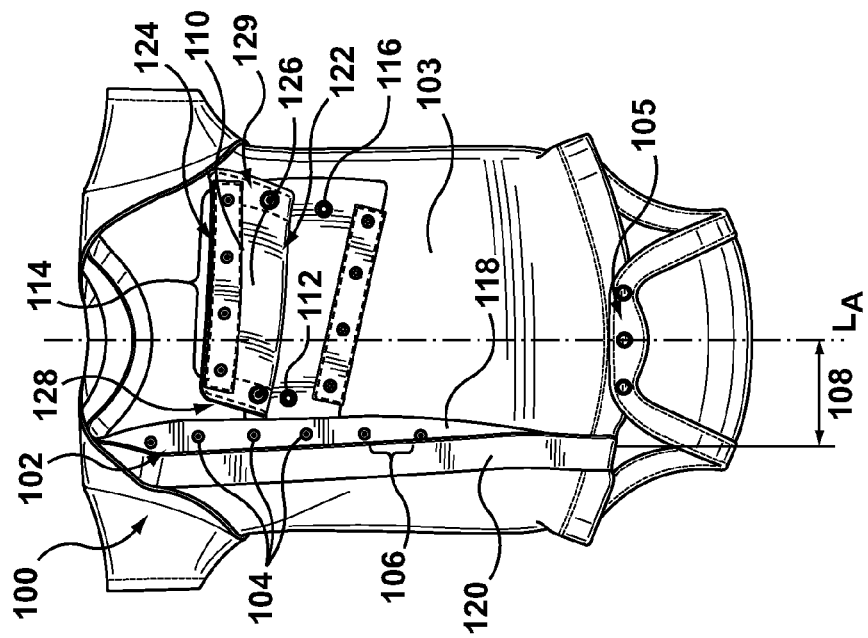
FIG. 2 is an image of the garment of FIG. 1, wherein the vertical opening and the flap of the garment are closed and a catheter is secured therein.

Referring FIGS. 1 and 2, a garment 100 including a front panel 103 is split along a vertical opening 102 defining a shirt underlap 118 and a shirt overlap 120. Underlap 118 and overlap 120 are detachably connected as described below and sometimes described as a placket. A transverse flap 110 on an outer surface of front panel 103 of garment 100 secures an external portion of a central line or catheter. FIG. 1 illustrates garment 100 having both opening 102 and flap 110 open, while FIG. 2 illustrates both opening 102 and flap 110 closed with a catheter secured therein, the ends of which are exposed or extending beyond closed flap 110. Closed opening 102 and flap 110 cooperate to secure an external portion of the catheter against movement and minimize irritation to the body at the exit site or dislodgment of a catheter and the position of its tip within the body. When opening 102 and flap 110 are closed, access to the exit site and to the external portion of the catheter inside garment 100 is effectively denied to the patient, so that he/she cannot reach or pull on the implanted catheter. In addition, garment 100 eliminates the need to tape the catheter to the patient's skin so problems of sores, rashes and potentials for infection are eliminated. Similarly, expenses for tape, bandages, gauze, antiseptic solutions and related items are eliminated.

As noted above, vertical opening 102 defines two longitudinal strips or segments of overlapping material, an outer strip or overlap 120 and an inner strip or underlap 118. A series of closure means or fasteners 104 having gaps or spaces 106 therebetween are provided to releasably couple overlap 120 and underlap 118 together, thereby closing vertical opening 102. Fasteners 104 may be, for example and not by way of limitation, snaps, hooks, buttons, or hook and loop fasteners. For example, if closure means 104 are snaps, the male disc of the snap may be placed on the inside surface of overlap 120 and the female disc of the snap may placed on the counter-facing, outside surface of underlap 118, or vice versa. Fasteners 104 may be secured to garment 100 in any suitable manner, including but not limited to sewing, adhesive, plying, or hammering using a specific punch and die set. In one embodiment, vertical opening 102 is horizontally offset 108 from the longitudinal or vertical central axis $L_A$ such that opening 102 is positioned over or near an exit site of the catheter in the chest of the body of the patient, which is displaced to the right of center on the body. Opening 102 may, however, be centered or be offset to left of center of the body. It will be understood by those of ordinary skill in the art that the number of fasteners utilized in series of fasteners 104 may vary according to the length of garment 100 and the desired spacing therebetween.

Flap 110 is a segment of material having a top edge 122 that is secured to front panel 103 of garment 100. In the embodiment shown, top edge 122 is sewn to front panel 103, but top edge 122 may be otherwise attached to front panel 103, including by releasable fasteners. More particularly, flap 110 is positioned adjacent to vertical opening 102 and adjacent to the exit site of the catheter in the chest of the body of the patient. Flap 110 may be preferably placed on the side of front panel 103 than includes underlap 118, as shown, such that overlap 120 covers the portion of the catheter extending over underlap 118, as shown in FIG. 2. Flap 110 extends across front panel 103 in a horizontal or transverse direction to vertical seam 102. In one embodiment, flap 110 extends across front panel 103 in a downward angle Ø relative to a horizontal or transverse axis $T_A$ of garment 100. Angle Ø may be between zero and 45 degrees and generally directs the external portion of the catheter towards the patient's hip so that it does not interfere with movement of the patient's arm. In one embodiment, flap 110 is generally rectangular and has a width $W_F$ and length $L_F$ (see FIG. 2) that effectively covers the external portion of the catheter when closed. In one embodiment, the width $W_F$ of flap 110 ranges between two and four inches and the length $L_F$ of flap 110 ranges between four and ten inches. It will be understood by those of ordinary skill in the art that the width of flap 110 may vary according to the size of the external portion of the catheter and the desired coverage thereof, and the length of flap 110 may vary according to the width of garment 100 and the desired coverage of the external portion of the catheter.

An inside surface 126 of flap 110 includes a series of closure means or fasteners 114 along a bottom edge 124 of the flap in order to releasably couple and close flap 110 onto front panel 103 of garment 100. When closed, flap 110 forms a pocket or space between an outside surface of front panel 103 of garment 100 and inside surface 126 of flap 110 in order to house and secure the external portion of the catheter. Fasteners 114 may be, for example, snaps, hooks, buttons, or hook and loop fasteners. For example, if closure means 114 are snaps, the male disc of the snap may placed on inside surface 126 of flap 110 and the female disc of the snap may placed on the counter-facing, outside surface of front panel 103 of garment 100, or vice versa. Fasteners 114 may be secured to garment 100 in any suitable manner, including but not limited to sewing, adhesive, plying, or hammering using a specific punch and die set. It will be understood by those of ordinary skill in the art that the number of fasteners utilized in series of fasteners 114 may vary according to the length of garment 100 and the desired spacing therebetween.

In addition to the series of closure means or fasteners 114, flap 110 is also releasably secured to front panel 103 of garment 100 via a stopper or tug guard 112 located on a side edge 128 of flap 110, adjacent to vertical opening 102, and a separator 116 located on the opposing side edge 129 of flap 110. Stopper 112 and separator 116 are fasteners such as snaps, buttons, or hook and loop fasteners that are secured to garment 100 in any suitable manner, including but not limited to sewing, adhesive, plying, or hammering using a specific punch and die set. In one embodiment, stopper 112 and separator 116 are larger fasteners than fasteners 104 and/or fasteners 114 such that more force is required to separate stopper 112 and separator 116 due to their functions described in more detail herein.

FIGS. 1 and 2 illustrate garment 100 in the form of a one-piece bodysuit to be worn by an infant or child, but the vertical opening and transverse flap may be applied to other articles of clothing, including but not limited to tee-shirts, tanktops, sweatshirts, sweaters, dresses, blouses, and undergarments. Garment 100 may be constructed from any suitable material, such as but not limited to a soft cotton material to maximize absorbency, comfort and washability. When in the form of a one-piece bodysuit for an infant or child, garment 100 is relatively close-fitting and may include a horizontal opening 105 at or near the crotch region and one or more closure means such as snaps, buttons, or hook and loop fasteners for closing the opening in order to change the child's diaper without removing the bodysuit.

Figure 3:
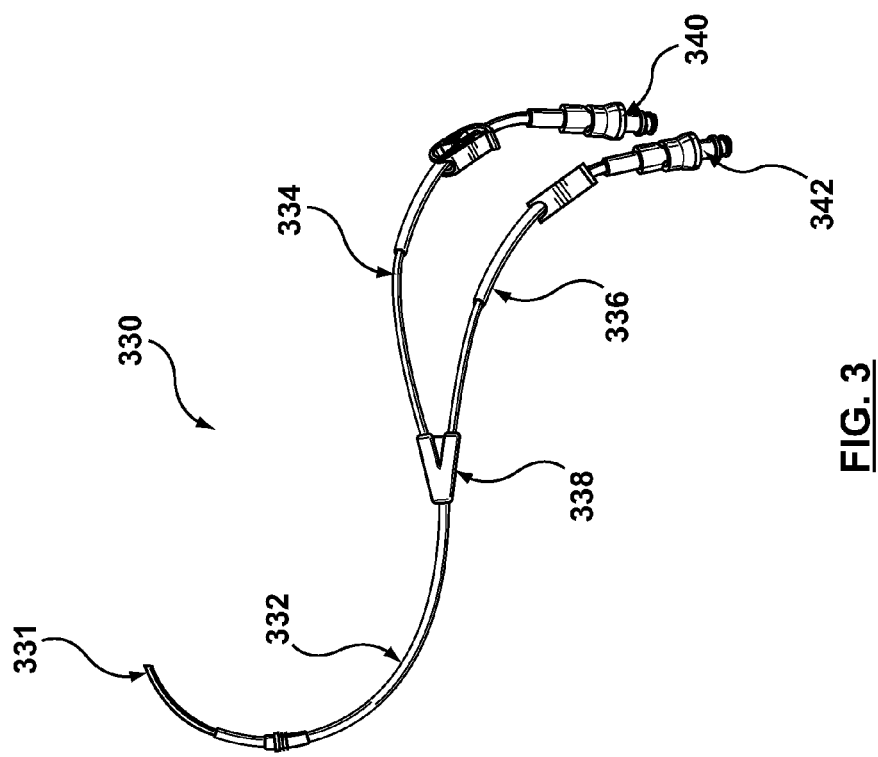
FIG. 3 is an image of biluminal catheter that may be utilized in embodiments hereof

Turning now to FIG. 3, an exemplary biluminal catheter 330 that is to be surgically implanted within a body of the patient is shown. Depending on its use, a central line catheter is monoluminal, biluminal or triluminal, depending on the actual number of tubes or lumens. In a biluminal catheter configuration, the catheter appears to be two separate or distinct tubular components outside or external to the body that meld or combine into one tubular component before entering the body. However, there is no communication between the two lumens of the catheter so that different medications, fluids, blood products can be infused at the same time. More particularly, catheter 330 includes a proximal end or tip 331 to be implanted within the body. For example, if catheter 330 is a central venous catheter such as the Hickman® catheter or Broviac® catheter, proximal end 331 is inserted into the large vein leading directly into the heart. Such catheters allow the delivery of drugs and other materials directly into the vascular system of a patient by placing the implanted end of the catheter into the superior vena cava with the tip of the catheter positioned to lie in the right atrium or lower superior vena cava.

Catheter 330 includes a proximal shaft 332 and first and second distal shaft branches 334, 336, respectively, that extend separately and independently from the distal end of proximal shaft 332 via a junction or divider 338. A portion of proximal shaft 334 extends within or is internal to the patient, while the remainder of proximal shaft 334, junction 338, and branches 334, 336 are external to and extend outside of the patients body. Proximal shaft 334 is biluminal having a first lumen (not shown) that fluidly communicates with a lumen defined by first distal shaft branch 334 and a second lumen (not shown) that communicates with a lumen defined by second distal shaft branch 336. First and second distal shaft branches 334, 336 include distal ends that may be enlarged and provided with removable closure caps 340, 342, respectively. When catheter 330 is to be used for infusing or withdrawing fluids from the body, caps 340, 342 are removed for this purpose and then replaced. Such use may take place at various times, and when the catheter is used only infrequently steps must be taken to maintain the lines free by administering heparin solution through the distal ends of catheter 330.

Figure 4:
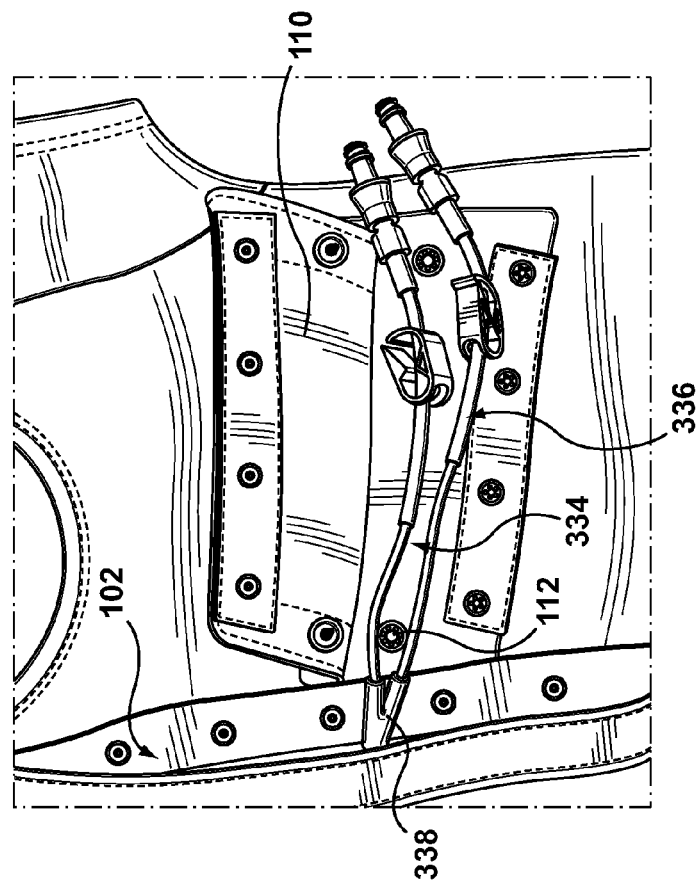

Turning now to FIGS. 4-6, a method of securing catheter 330 via garment 100 is described. In FIG. 4, catheter 330 is shown extending through open vertical opening 102 and over front panel 103 of garment 100. Although flap 110 is shown in an open position and not yet secured over catheter 330, first and second distal branches 334, 336 of catheter 330 extend over garment 100 at a location that will be covered by flap 110 when flap 110 is closed. As previously mentioned with respect to FIG. 1, vertical opening 102 may be horizontally offset 108 from the longitudinal or vertical central axis $L_A$ such that opening 102 is positioned over or near the exit site of the catheter. Catheter 330 extends from an exit site on the body and through a gap 106 between a pair fasteners 104 at overlap 120/underlap 118. Since the series of fasteners 104 define a gap 106 between each pair of fasteners 104, there are several gaps 106 that are candidates or options for the pass-through location of catheter 330. Thus, the pass-through location of garment 100 is adjustable. It may be desirable to pass catheter 330 through the gap located adjacent to flap 110. In addition, when opened and spread apart, the series of fasteners 104 give a caregiver convenient access to the patient's entire upper and mid torso without removing garment 100, disconnecting catheter 330, or disturbing the patient. Further, garment 100 may easily be removed and replaced without disconnecting catheter 330.

Referring to FIG. 5, in order to secure catheter 330, stopper 112 (obscured or closed in FIG. 5) is fastened to garment 100 such that stopper 112 is located between first and second distal branches 334, 336. Notably, junction 338 is located between the exit site of catheter 330 and stopper 112. Stopper 112 provides anti-tug protection that reduces the risk of unintentional dislodgement of implanted proximal end 331 of catheter 330 while distal branches 334, 336 of catheter 330 are exposed and/or being accessed. More particularly, if one or both of distal branches 334, 336 are pulled or tugged, junction 338 is pressed against stopper 112 and limits further motion of catheter 330.

Next, referring to FIG. 6, separator 116 (obscured or closed in FIG. 6) is fastened to garment 100 such that stopper 112 is located between first and second distal branches 334, 336. Separator 116 creates two passageways within the pocket or space formed between garment 100 and closed flap 110, and the two channels or conduits accommodate first and second distal branches 334, 336, respectively. Accordingly, the distal branches do not become tangled while being housed under closed flap 110 which is important so that the caregiver does not inadvertently mistake or mix up the distal branches when administering medication, fluid, or taking samples. In addition, separator 116 also provides additional anti-tug protection that prevents unintentional dislodgement of implanted proximal end 331 of catheter 330 because the two channels created by separator 116 snuggly surround capped distal ends 340, 342 of first and second distal branches 334, 336, respectively. Lastly, when separator 116 is closed and catheter 330 is not in use, separator 116 may be used to effectively seal the side of flap 110 to garment 100 and retain catheter 330 within the pocket formed by a closed flap 110. Since a patient with implanted catheter 330 may need not be subject to treatment over extended periods of time, it is important that the external portions of catheter 330 be stored out of sight and securely retained for permitting the desired freedom of the patient, while still making its use readily available should the need arise. Those skilled in the art would recognize that the steps noted above need not be performed in the order described.

Referring back to FIG. 2, catheter 330 is secured by closing fasteners 114 in order to close flap 110. Series of fasteners 104 may also be fastened in order to close opening 102, although closure of opening 102 may occur at any point during the above-described method. Further, those skilled in the art would recognize that the other steps described above for securing catheter 330 may be performed in any reasonable order. Once flap 110 is closed, distal branches 334, 336 may extend in a lateral direction across garment 100 such that capped distal ends 340, 342 protrude out from the side of flap 110 as shown in FIG. 2. By extending beyond flap 110, capped distal ends 340, 342 are exposed and may be easily accessed by a caregiver such as medical personnel, parents, or others. Alternatively, capped distal ends 334, 336 may be coiled or tucked into the pocket or space formed between front panel 103 and closed flap 110 so that the entire external portion of catheter 330 is stored out of sight.

Figure 7:
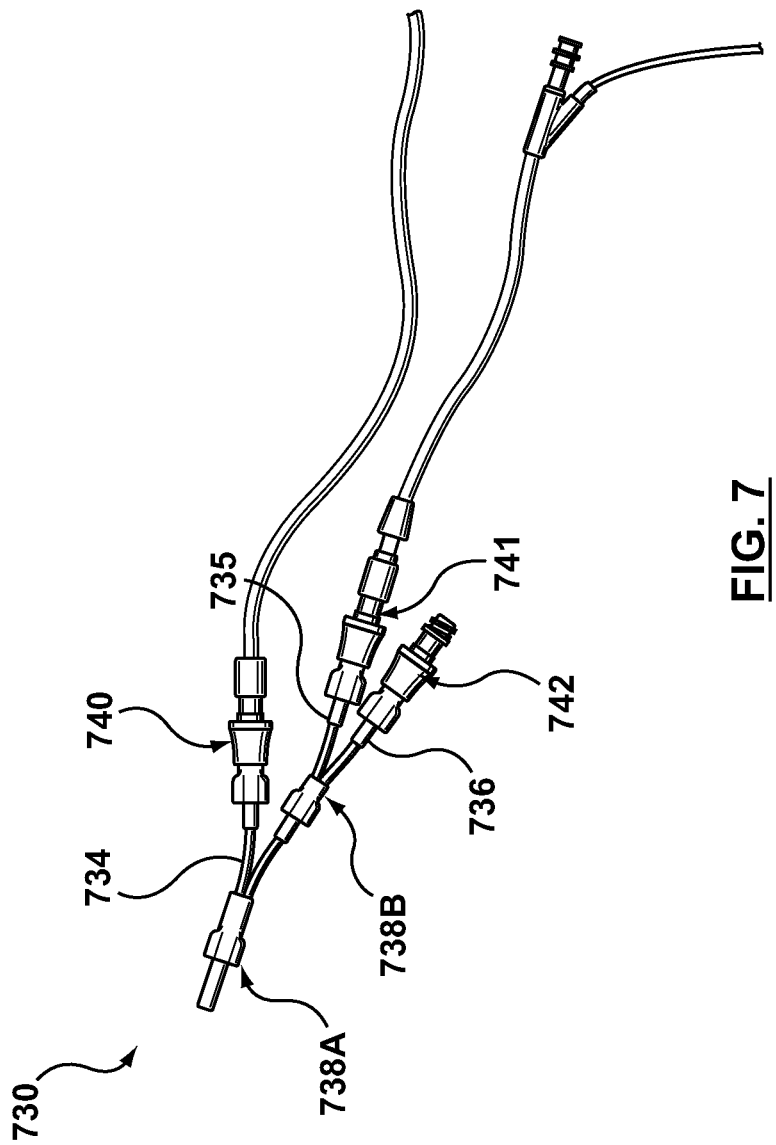
FIG. 7 is an image of catheter having three lumens that may be utilized in embodiments hereof.

Although described for securing a biluminal catheter, garment 100 may also be utilized to secure other implanted catheters having external portions for administering medication, fluids, or the like. For example, FIG. 7 illustrates a triluminal catheter 730 having three lumens. In a catheter having three lumens, the catheter appears to be three separate or distinct tubular components outside of the body that meld or combine into one tubular component before entering the body. However, there is no communication between the three lumens of the catheter so that different medications, fluids, blood products can be infused at the same time. More particularly, similar to catheter 330, catheter 730 includes a proximal shaft (not shown in FIG. 7) having a proximal end or tip to be implanted within the body. An external portion of catheter 730 is shown in FIG. 7 and includes first, second, and third distal shaft branches 734, 736, 735, respectively, that extend separately and independently from the distal end of proximal shaft 732 via two junctions or dividers 738A and 738B. Proximal shaft 734 is triluminal having a first lumen (not shown) that fluidly communicates with a lumen defined by first distal shaft branch 734, a second lumen (not shown) that communicates with a lumen defined by second distal shaft branch 736, and a third lumen (not shown) that communicates with a lumen defined by third distal shaft branch 735. Distal shaft branches 734, 736, 735 include distal ends that each may be enlarged and provided with removable closure caps 740, 742, 741, respectively.

Figure 9:
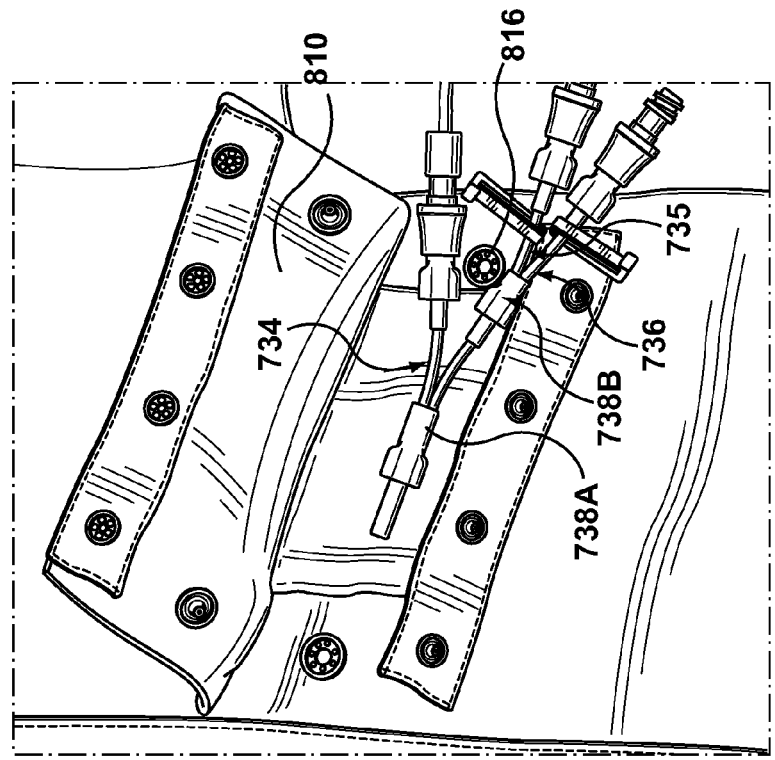
FIGS. 8-9 are images that illustrate how the catheter of FIG. 7 is secured within a garment according to an embodiment hereof.
Figure 8:
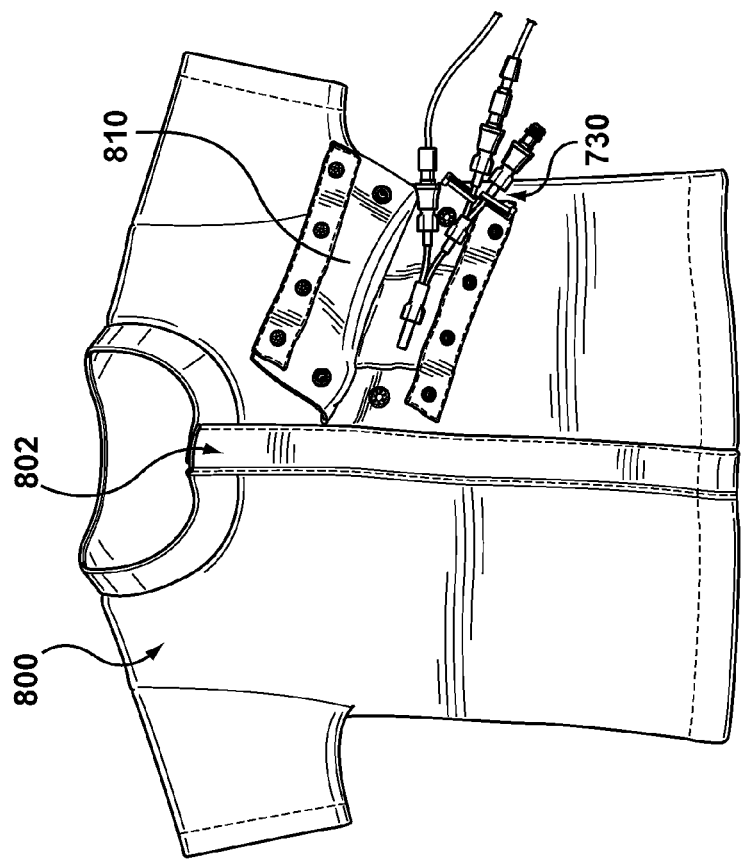

Turning now to FIGS. 8-9, catheter 730 is shown placed over a garment 800 for securement thereto. In this embodiment, garment 800 is a tee-shirt having a vertical opening 802 down the longitudinal centerline of garment 800 and a flap 810 extending transversely across the left side of garment 800. In this embodiment, in order to secure catheter 830, separator 816 is fastened to garment 800 such that separator 816 is located between first distal branches 734 and second and third distal branches 736, 735. Notably, junction 738 is located between the exit site of catheter 730 and separator 816. Separator 816 provides anti-tug protection that prevents unintentional dislodgement of the implanted proximal end of catheter 730 while distal branches 734, 736, 735 of catheter 730 are exposed and/or being accessed. More particularly, if one or more of distal branches 734, 736, 735 are pulled or tugged, junction 738 is pressed against separator 816 and limits further motion of catheter 730.

While various embodiments according to the present invention have been described above, it should be understood that they have been presented by way of illustration and example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:

1. A garment for securing an external portion of a catheter having a single proximal shaft that transitions to at least two distal branches via a junction, the garment comprising:
    an opening extending vertically along a front panel of the garment, the opening including a first series of fasteners for releasably closing the opening, wherein the first series of fasteners have spaces therebetween configured to allow the catheter to pass therethrough;
    a flap coupled to an exterior surface of the front panel of the garment, the flap extending across the front panel in a direction generally transverse to the vertical opening, wherein the flap is positioned adjacent to the vertical opening and includes a second series of fasteners for releasably coupling a free edge of the flap onto the front panel to form a pocket between the exterior surface of the front panel and an interior surface of the flap, the pocket configured to enclose the external portion of the catheter between the exterior surface of the front panel and the interior surface of the flap when the flap is closed; and
    a stopper coupled to flap and positioned to releasably fasten the flap to the front panel between the distal branches of the catheter and adjacent to the junction of the catheter.

2. The garment according to claim 1, wherein the vertical opening is defined by an outer strip and an inner strip of overlapping material, and the first series of fasteners for releasably closing the opening couple the outer strip and the inner strip together.

3. The garment according to claim 1, wherein the vertical opening is horizontally offset from a central longitudinal axis of the garment.

4. The garment according to claim 1, wherein the flap is a segment of material having a top edge that is secured to the exterior surface of the front panel of the garment and the free edge of the flap is a bottom edge of the flap.

5. The garment according to claim 4, wherein the stopper is located approximately midway between the top edge and the bottom edge of the flap.

6. The garment according to claim 4, wherein the flap extends across the front panel in a downward angle between zero and 45 degrees relative to a horizontal axis of the garment.

7. The garment according to claim 1, wherein the stopper is located on a first side edge of the flap adjacent to the vertical opening.

8. The garment according to claim 7, wherein a separator fastener is located on a second side edge of the flap opposite the first side edge.

9. The garment according to claim 8, wherein the stopper and the separator fastener are located between a top edge of the flap and the free edge of the flap.

10. The garment according to claim 1, wherein the stopper is a fastener that requires more force to separate than the second series of fasteners for releasably coupling the free edge of the flap onto the front panel.

11. The garment according to claim 1, wherein the garment is a one-piece bodysuit.

12. The garment according to claim 1, wherein the garment is a tee-shirt.

13. A garment for securing an external portion of a catheter, the garment comprising:

an opening extending vertically along a front panel of the garment, the opening including a first series of fasteners for releasably closing the opening, wherein the first series of fasteners have spaces therebetween configured to allow the catheter to pass therethrough;

a flap coupled to an exterior surface of the front panel of the garment, the flap extending the front panel in a direction generally transverse to the vertical opening, wherein the flap is positioned adjacent to the vertical opening and includes a second series of fasteners for releasably coupling a free edge of the flap onto the front panel to form a pocket between the exterior surface of the front panel and an interior surface of the flap, the pocket configured to enclose the external portion of the catheter between the exterior surface of the front panel and the interior surface of the flap when the flap is closed; and a stopper coupled to the flap and positioned adjacent the opening and between the free edge of the flap and an opposing edge of the flap, wherein the stopper releasably fastens the flap to the front panel between the second series of fasteners and the opposing edge of the flap.

14. The garment according to claim 13, wherein the vertical opening is defined by an outer strip and an inner strip of overlapping material, and the first series of fasteners for releasably closing the opening couple the outer strip and the inner strip together.

15. The garment according to claim 13, wherein the flap is a segment of material, wherein the opposing edge of the flap is a top edge that is secured to the exterior surface of the front panel of the garment and the free edge is a bottom edge of the flap.

16. The garment according to claim 15, wherein the stopper is located approximately midway between the top edge and the bottom edge of the flap.

17. The garment according to claim 15, wherein the flap extends across the front panel in a downward angle between zero and 45 degrees relative to a horizontal axis of the garment.

18. The garment according to claim 1, wherein the stopper is located on a first side edge of the flap adjacent to the vertical opening, and a separator fastener is located on a second side edge of the flap opposite the first side edge.

19. The garment according to claim 1, wherein the stopper is a fastener that requires more force to separate than the second series of fasteners for releasably coupling the free edge of the flap onto the front panel.

20. A method of securing an external portion of a catheter having a single proximal shaft that transitions to at least two distal branches via a junction, the method comprising the steps of:

passing the at least two external distal branches of the catheter through a space between a pair of fasteners that releasably close a vertical opening that extends down a front panel of a garment, wherein the garment further includes a flap coupled to an exterior surface of the front panel and positioned adjacent to the vertical seam, the flap extending across the exterior surface of the front panel in a direction generally transverse to the vertical opening;

fastening a stopper located on the flap to the exterior surface of the front panel of the garment such that the stopper is located between the distal branches of the catheter and adjacent to the junction of the catheter, wherein the stopper reduces the risk of unintentional dislodgement of the catheter; and fastening a series of fasteners located on a free edge of the flap onto the front panel of the garment in order to enclose the external portion of the catheter under the flap between an interior surface of the flap and the exterior surface of the front panel.

\* \* \* \* \*